United States Patent

Casati et al.

Patent Number: 4,664,852
Date of Patent: May 12, 1987

[54] PROCESS FOR THE PREPARATION OF L-CARNITINE

[75] Inventors: Paolo Casati, Monza; Claudio Fuganti, Milan, both of Italy

[73] Assignee: Sclavo S.p.A., Siena, Italy

[21] Appl. No.: 866,144

[22] Filed: May 22, 1986

[30] Foreign Application Priority Data

May 24, 1985 [IT] Italy ................. 20889 A/85

[51] Int. Cl.$^4$ ........................................ C07C 101/12
[52] U.S. Cl. ................... 260/501.13; 560/20; 560/23; 560/184
[58] Field of Search ............. 260/501.13; 560/184

[56] References Cited

U.S. PATENT DOCUMENTS

| | | | |
|---|---|---|---|
| 3,135,788 | 6/1964 | Noguchi et al. | 260/501.13 |
| 3,151,149 | 9/1964 | Strack et al. | 260/501.13 |
| 3,468,937 | 9/1969 | Strack et al. | 260/501.13 |

FOREIGN PATENT DOCUMENTS

| | | | |
|---|---|---|---|
| 0169614 | 1/1986 | European Pat. Off. | 260/501.13 |
| 2518813 | 11/1975 | Fed. Rep. of Germany | 260/501.13 |
| 2101133 | 1/1983 | United Kingdom | 260/501.13 |
| 2132614 | 7/1984 | United Kingdom | 560/184 |

*Primary Examiner*—J. E. Evans
*Attorney, Agent, or Firm*—Hedman, Gibson, Costigan & Hoare

[57] ABSTRACT

A process for preparing L-carnitine (I) wherein
(a) diketene (II) is reacted with chlorine, and the chlorination product thus obtained is submitted to amidation by the methylester of an optically-active aminoacid, having formula:

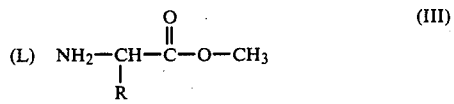

wherein $R=CH_2A_r$ or $A_r$ wherein Ar is a substituted or not-substituted aromatic group, to yield the compound 4-chloro-3-ketobutyrylamide of the methylester of the optically-active aminoacid: (IV)

(b) the compound (IV) is reduced in the presence of a reducing agent to yield a mixture (V) of (3R)-4-chloro-3-hydroxybutyrylamide of the methylester of an optically-active acid (VI), and (3S)-4-chloro-3-hydroxybutyrylamide of the methylester of an optically active aminoacid (VII), (c) the compound (VI) is separated and recovered from the reduction reaction product, (d) the compound (VI) is submitted to methanolysis by hydrogen chloride gas in methanol, (e) the methylester of the optically-active aminoacid (III) is precipitated and recovered from the methanolysis reaction product, (f) from the mother liquors the methylester of (3R)-4-chloro-3-hydroxybutyric acid (VIII) is recovered, (g) the compound (VIII) thus obtained is treated with trimethylamine in ethanol, is hydrolyzed with hydrochloric acid and L-carnitine is separated and recovered.

16 Claims, No Drawings

PROCESS FOR THE PREPARATION OF L-CARNITINE

The present invention relates to the production of β-hydroxy-γ-trimethylamino-butyric acid (L-carnitine)

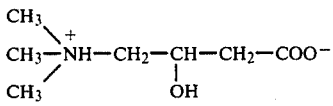
(I)

L-Carnitine (I), to which the R-configuration corresponds, also known as Vitamine B$_t$, is a hydroxyaminoacid present in animal tissues, and stimulates the mitochondrial oxidation of fatty acids, producing energy at muscular level.

Generarally, L-carnitine is used in the pharmaceutical field as reconstituent agent.

Recently, the correlation has been demonstrated between the deficiency of carnitine and some diseases associated to disorders of lipidic metabolism, characterized by an increase of triglycerides and by the accumulation of long-chain fatty acids.

It has been found that the administering of L-carnitine in such therapeutical fields as: the chronic hemodialisis, the correction of lipiproteinic pattern, the suppression of cardiac arrythmia with a heart infarction being in progress, and the infusional therapy, normalizes the metabolic equilibrium.

In the art various processes are known for the chemical synthesis of carnitine and of its derivatives.

According to U.S. Pat. No. 3,135,788, D,L-carnitine is prepared by a process comprising placing the compound epihalohydrin of formula:

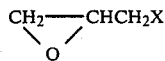

wherein X=Cl, Br or I, in contact with trimethylamine, the reaction product obtained, 3-halo-2-oxypropyl-trimethylammonium chloride, being reacted with sodium cyanide or potassium cyanide, the compound 3-cyano-2-oxypropyl-trimethylammonium chloride obtained being isolated, and hydrolyzed under room pressure, and finally the compound D,L-carnitine hydrochloride being isolated.

According to Carter and Blattacharye [J. Amer. Chem. Soc 75, 2503 (1953)], D,L-carnitine is obtained by reacting benzaldehyde, epichlorohydrin and ammonia in an organic solvent, the reaction product 2-phenyl-5-chloromethyloxazolidine is isolated and said compound is subsequently transformed into D,L-carnitine according to known techniques, with a yield of 20–25%.

These processes of the prior art give rise, besides the L-isomer, to the formation of D-carnitine isomer, the presence of which is undesirable.

Fritz et al. [J. Biol. Chem. 240, 2188 (1965)] have in fact observed that D-carnitine inhibits the activity of L-carnitine and treatments are hence required to the purpose of separating and purifying the desired product.

The separation of the two isomers of the racemic mixture can be carried out by an enzymatic process, or by the classic optical resolution.

French Pat. No. FR 2,398,046 discloses and claims a process for the preparation of L-carnitine by the oxidation of the racemic mixture to corresponding 3-ketoderivatives and subsequent stereospecific reduction to chlorinated L-carnitine by the use of enzymatic systems induced in Pseudomonas.

According to the classic optical resolution techniques, the derivatives of D,L -carnitine or of intermediates of the synthesis thereof are separated by fractional crystallization of salts with resolving agents suitable to that purpose. In the prior art as the resolving agents optically-active acids such as, e.g., D-tartaric acid and dibenzoyl-D-tartaric acid [Ayata, Yakugaku Sashi 81, 778, 1961], a mixture of D-camphoric-10-sulphonic acid and dibenzoyl-D-tartaric acid [E. Strack et al., Z. Physiol. Chem. 318, 129 (1960)] or D-camphoric acid (Sigma-Tau, IT 50224 A/78) have been used.

However, by operating according to the methods as described by Ayata and Stack, L-carnitine chloride is obtained with a yield of about 10%, because the two chlorides are difficult to be separated.

B. Zhan et al. [J. Am. Chem. Soc. 105, 5925–5926 (1983)] describe a method for the preparation of L-carnitine by the stereospecific microbial reduction of 4-chloro-3-ketobutyric acid (Cl—CH$_2$—CO—CH$_2$—COOR) ester to (3R)-4-chloro-3-hydroxybutyric acid ester. Such an operating way suffers however from limitations which render the same process disadvantageous from the economic point of view and anyway not much suitable to be applied on full industrial scale.

In fact, by operating with a high substrate/biomass ratio, which is the most convenient from an economic viewpoint, in addition to the desired R-isomer, considerable amounts are formed of difficult-to-be-separated S-isomer.

Furthermore, the stereospecificity of the reaction is influenced by the number of carbon atoms in ester group.

Summing-up, the processes of the prior art are expensive, due to the use of valuable starting materials, due to the number of required steps, and due to the poor overall yields.

The purpose of the present invention is hence a process for the production of L-carnitine free, or substantially free, from the drawbacks above mentioned.

In particular, the purpose of the present invention is a process allowing the reaction to be contolled towards the formation of L-isomer of carnitine.

The present invention is essentially grounded on the observation that the (R)-4-chloro-3-hydroxybutyric compound, useful for the preparation of L-carnitine, can be easily obtained in a cheap way, by optical resolution, by using as the optically resolving agent the methylester of an optically-active aminoacid.

Accordingly, according to the present invention, L-carnitine

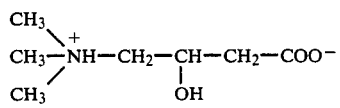
(I)

is prepared by a process characterized in that
(a) the compound diketene having formula:

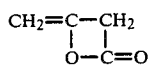 (II)

is reacted with chlorine,
and the chlorination product thus obtained is submitted to amidation by the methylester of an optically-active aminoacid, having formula:

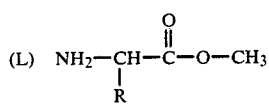 (III)

wherein R=CH₂Aᵣ or Aᵣ is a substituted or not-substituted aromatic group,
to yield the compound 4-chloro-3-ketobutyrylamide of the methylester of the optically-active aminoacid:

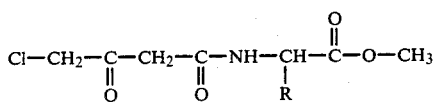 (IV)

wherein R has the above reported meaning,
 (b) the compound (IV) is reduced in the presence of a reducing agent to yield the compound

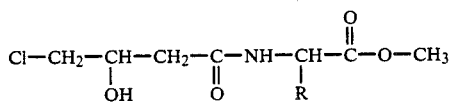 (V)

wherein R has the above reported meaning, in the form of a mixture of (3R)-4-chloro-3-hydroxybutyrylamide of the methylester of an optically-active aminoacid (VI) and (3S)-4-chloro-3-hydroxybutyrylamide of the methylester of an optically active aminoacid (VII),
 (c) the compound (3R)-4-chloro-3-hydroxybutyrylamide of the methyl ester of an optically-active aminoacid (VI) is separated and recovered from the reduction reaction product,
 (d) the compound (VI) is submitted to methanolysis by hydrogen chloride gas in methanol,
 (e) the methylester of the optically-active aminoacid (III) is precipitated and recovered from the methanolysis reaction mixture,
 (f) from the mother liquors the compound methylester of (3R)-4-chloro-3-hydroxybutyric acid having formula

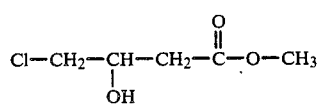 (VIII)

is recovered,
 (g) the compound (VIII) thus obtained is treated with trimethylamine in ethanol, is hydrolyzed with hydrochloric acid and the compound L-carnitine (I) is separated and recovered.

STEP (A)

In the step (a) of the process of the present invention, the compound diketene having formula:

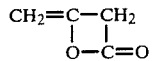 (II)

is reacted with chlorine.

The chlorination reaction is carried out in the liquid phase, with the components being dissolved in an inert organic solvent and in an equimolecular ratio to each other, at a temperature of from −20° C. to +40° C., for a time of from 20 minutes to 12 hours.

Preferably, the reaction is carried out at a temperature of −20° C. for 30 minutes. Organic solvents suitable to the purpose are selected among hydrocarbons, esters and ethers.

Typically, methylene chloride is used.

The chlorinated compound thus obtained is then submitted to an amidation reaction by the methylester of an aminoacid, of formula:

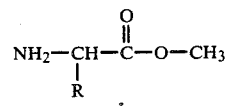 (III)

wherein R is preferably a group

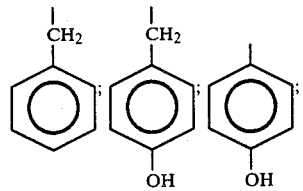

to yield the compound 4-chloro-3-ketobutyrylamide of the methyl ester of optically-active aminoacid, with formula:

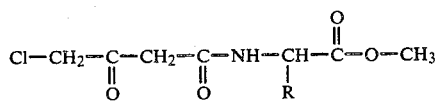 (IV)

wherein R has the meaning reported above.

The amidation reaction is carried out in the liquid phase in the same solvent as of the chlorination reaction, in the presence of trimethylamine, at a temperature of from −0° C. to +40° C., for a time of from 30 minutes to 12 hours.

The reaction is generally carried out at 0° C. within a time of about 1 hour.

STEP (B)

In the step (B) of the present invention, the compound (IV) is submitted to a reduction reaction by using a reducing agent to yield the compound of formula

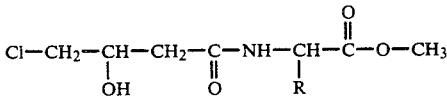 (V)

wherein R has the above reported meaning, in the form of a mixture of (3R)-4-chloro-3-hydroxybutyrylamide of the methylester of an optically-active acid and (3S)-4- chloro-3-hydroxybutyrylamide of the methyleser of an optically-active aminoacid.

Reducing agents suitable to that purpose are selected from the hydrides of alkali metals.

Preferably, sodium borohydride (NaBH$_4$) is used.

The reduction reaction is carried out at a temperature of from $-20°$ C. to $+40°$ C. for a time of from 20 minutes to 12 hours, the operating conditions being typically a temperature of $0°$ C. for 2 hours.

STEP (C)

In step (C) the separation of the two isomers (VI) and (VII) from the reaction mixture is then carried out.

To that purpose, a whatever technique of the prior art can be used, such as, e.g., fractional crystallization from organic solvents, such as ethyl acetate, hexane, water or alcohols, High Pressure Liquid Chromatography, or chromatography on silica gel column.

Typically, the separation is carried out by crystallization from boiling ethyl acetate, the solution being kept at 0° C. overnight. By operating in such a way, the compound (3R)-4-chloro-3-hydroxybutyrylamide of the methylester of optically-active aminoacid (VI) is easily separated with a yield of 35-45%.

Upon analysis, the compound appears to be free from impurities.

STEP (D)

In step (D), the compound (3R)-4-chloro-3-hydroxybutyrylamide of the methylester of the optically-active aminoacid is submitted to methanolysis in the presence of hydrogen chloride gas.

In particular, the reaction is carried out in a liquid medium, in methanol saturated with hydrogen chloride gas and maintaining the resulting solution under boiling conditions, in a reflux equipment for a 24-hours time.

At the end of such time period, the volume of the reaction mixture is reduced under reduced pressure and the methylester of the optically-active aminoacid (III) is precipitated off, by the addition of an equal volume of ethyl ether.

The precipitated product is then filtered off, with a yield of 70-75%.

The compound (III) so recovered is recycled to the synthesis process. The filtrate is concentrated to dryness and is redissolved with ethyl acetate.

The solvent is then evaporated off from the solution thus obtained, and the compound methylester of (3R)-4-chloro-3-hydroxybutyric acid (VIII) is thus obtained with a yield of 60-65%.

In the step (G), the compound (VIII) is finally transformed into L-carnitine, so as reported in J. Amer. Chem. Soc 105, 5925 (1983). In particular, the compound (VIII) is reacted overnight with trimethylamine in ethanol, in a closed vessel, at a temperature of 80° C.

The solution is cooled to room temperature, the solvent is evaporated to dryness, and the residue is taken up with a solution of hydrochloric acid at 10% (v/v) in water.

The mixture thus obtained is kept under boiling conditions, in a reflux equipment, for about 2 hours.

The separation of L-carnitine is then carried out by crystallization from ethanol-acetone (1:2, v/v), and a product with $[\alpha]_D^{23}=29°-33°$ (c=2, H$_2$O) is obtained with a yield of from 31 to 35%.

The following Examples are illustrative and not limitative of the invention.

EXAMPLE 1

Preparation of (3R)-4-chloro-3-hydroxy-butyrylamide of L-phenylalanine methylester Into a glass flask, of 2 liters of capacity, equipped with stirring means, 682 g (1 mol) of diketene dissolved in 100 ml of anhydrous methylene chloride cooled to a temperature of $-20°$ C. and 75 g (1 mol) of chlorine dissolved in 200 ml of methylene chloride are charged. The mass inside the flask is stirred until a solution is obtained, and is reacted at $-20°$ C. for 30 minutes. To said stirred solution, 180 g (1 mol) of L-phenylalanine methylester dissolved in 400 ml of methylene chloride and 101 g (1 mol) of triethylamine are added.

The solution thus obtained is kept at 0° C. for one hour.

At the end of said time period, the solution is charged into a separation funnel and is washed twice, each time with 100 ml of water. The organic phase is separated and is diluted with an equal volume of methanol. To the resulting solution, over a time period of about 1 hour, 10 g of sodium borohydride is added, with the temperature being controlled at values of 0° C.

The reduction reaction is then carried out at a temperature of about 0° C. for a 2-hours time.

At the end of said reaction time, the volume is concentrated to the half, under reduced pressure, and the resulting solution is diluted with 200 ml of ethyl acetate.

The solution is then washed twice, each time with 100 ml of water, the washing liquors are separated, and from the reaction mixture the solvent is evaporated to dryness.

The residue thus obtained is crystallized from 500 ml of boiling ethyl acetate, the solution being kept at 0° C. overnight.

An amount of 140 g is thus obtained of (3R)-4-chloro-3-hydroxybutyrylamide of the methylester of L-phenylalanine (VI) with $[\alpha]_D^{20}=+63°$ (c=1, CHCL$_3$).

The product thus obtained is recrystallized twice as reported above, and 40 g is obtained of product (VI) with $[\alpha]_D^{20}=+77.5°$ (c=1, CHCL$_3$).

EXAMPLE 2

Preparation of L-carnitine

Into a solution of 40 g (0.15 mol) of (3R)-4-chloro-3-hydroxybutyrylamide of L-phenylalanine methyl ester, obtained as in Example 1, in 300 ml of methanol, hydrogen chloride gas is bubbled for a time of about 10 minutes.

The resulting solution is kept boiling, in a reflux equipment, for a 24-hours time.

At the end of said time the solution is concentrated under reduced pressure, is cooled, and to it an equal volume of ethyl ether is added.

In such a way, crystals of L-phenylalanine methylester hydrochloride (III) precipitate, and are filtered off. An amount of 22 g of compound (III) is obtained, with a yield of 70-75%.

The filtrate is then evaporated to dryness, is diluted with 50 ml of ethyl acetate, and is washed twice, each time with 20 ml of water; by so doing, the residual phenylalanine methylester hydrochloride is recovered.

Ethyl acetate is then evaporated off from the organic solution and 12 g (60-65%) is obtained of methyl ester of 4-chloro-3-hydroxybutyric acid (VIII) with $[\alpha]_D^{20}=-22°$ (c=1.5, CHCL$_3$).

An amount of 12 g of compound (VIII) is then treated overnight with 2 mol-equivalents of trimethylamine in 50 ml of ethanol, in closed vessel, at 80° C.

At the end of said reaction time, the solution is cooled to room temperature, the solvent is evaporated to dryness, the residue is diluted with 100 ml of 10% aqueous hydrochloric acid, and the resulting solution is kept boiling, in a reflux equipment, for 2 hours.

The solvent is then evaporated to dryness, the residue is diluted with water, is passed over a basic resin, and L-carnitine is crystallized from ethanol-acetone (1:2, v/v), at 0° C., overnight.

L-Carnitine is obtained with a yield of 35% and $[\alpha]_D^{23} = 29°-31°$ (c=2, H$_2$O).

EXAMPLE 3

Preparation of (3R)-4-chloro-3-hydroxybutyrylamide of L-tyrosine methylester

The process is the same as of foregoing Example 1, by using 196 g (1 mol) of L-tyrosine methylester.

An amount is thus obtained of 100 g of (3R)-4-chloro-3-hydroxybutyrylamide of L-tyrosine methylester with $[\alpha]_D^{20} = +15.5°$ (c=1, methanol). The compound, submitted to sequential crystallizations, shows the same optical activity.

EXAMPLE 4

An amount of 100 g of (3R)-4-chloro-3-hydroxybutyrylamide of L-tyrosine methylester is submitted to methanolysis under the same operating conditions as reported in Example 2. An amount is obtained of 20 g (70%) of (3R)-4-chloro-3-hydroxybutyric acid methylester with $[\alpha]_D^{20} = -23°$ (c=1.5 in CHCL$_3$). (3R)-4-Chloro-3-hydroxybutyric acid methylester is treated with trimethylamine and L-carnitine is obtained (yield 32%).

EXAMPLE 5

Preparation of (3R)-4-chloro-3-hydroxybutyrylamide of L-para-hydroxyphenylglycine methylester The process is carried out as described in foregoing Example 1, by using 1 mol of L-p-hydroxyphenylglycine methylester.

An amount is obtained of 120 g of (3R)-4-chloro-3-hydroxybutyrylamide of L-p-hydroxyphenylglycine methylester with $[\alpha]_D^{20} = +130.5°$ (c=1, MeOH).

This product, submitted to sequential crystallizations, displays the same optical power.

By submitting it to methanolysis, as reported in Example 2, L-p-hydroxyphenylglycine methylester and the compound (3R)-4-chloro-3-hydroxybutyric acid methylester with $[\alpha]_D^{20} = -23°$ (c=1, MeOH) are obtained.

We claim:
1. Process for the preparation of β-hydroxy-γ-trimethylaminobutyric acid (L-carnitine)

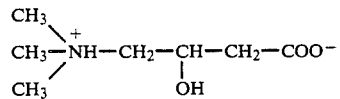

characterized in that
(a) the compound diketene having formula:

is reacted with chlorine, and the chlorination product thus obtained is submitted to amidation by the methylester of an optically-active aminoacid, having formula:

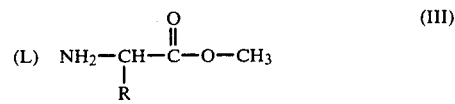

wherein R=CH$_2$A$_r$ or A$_r$ wherein Ar is a substitued or not-substituted aromatic group, to yield the compound 4-chloro-3-ketobutyrylamide of the methylester of the optically-active aminoacid:

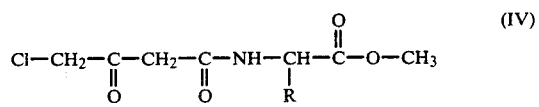

wherein R has the above reported meaning,
(b) the compound (IV) is reduced in the presence of a reducing agent to yield the compound

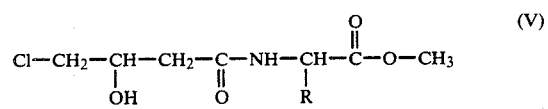

wherein R has the above reported meaning, in the form of a mixture of (3R)-4-chloro-3-hydroxybutyrylamide of the methylester of an optically-active aminoacid (VI) and (3S)-4-chloro-3-hydroxybutyrylamide of the methylester of an optically active aminoacid (VII),
(c) the compound (3R)-4-chloro-3-hydroxybutyrylamide of the methyl ester of an optically-active aminoacid (VI) is separated and recovered from the reduction reaction product,
(d) the compound (VI) is submitted to methanolysis by hydrogen chloride gas in methanol,
(e) the methylester of the optically-active aminoacid (III) is precipitated and recovered from the methanolysis reaction mixture,
(f) from the mother liquors the compound methylester of (3R)-4-chloro-3-hydroxybutyric acid having formula

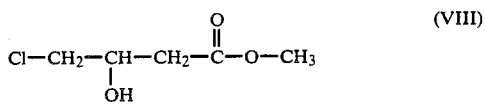

is recovered,
(g) the compound (VIII) thus obtained is treated with trimethylamine in ethanol, is hydrolyzed with hydrochloric acid and the compound L-carnitine (I) is separated and recovered.

2. Process according to claim 1, wherein R in compounds (III), (IV) and (V) is CH$_2$Ar.

3. Process according to claim 1, wherein the chlorination reaction in step (a) is carried out in the liquid phase, in an inert organic solvent, at a temperature of from −20° C. to +40° C. and for a time of from 20 minutes to 12 hours, with the two reactants being in equimolecular ratio to each other.

4. Process according to claim 1, wherein the amidation reaction in step (a) is carried out in the liquid phase, in an inert organic solvent, at a temperature of from −20° C. to +40° C. and for a time of from 20 minutes to 12 hours.

5. Process according to claims 3 and 4, wherein the organic solvent is selected from hydrocarbons, ethers and esters.

6. Process according to claim 5, wherein the organic solvent is methylene chloride.

7. Process according to claim 3, wherein the reaction is carried out at a temperature lower than 0° C. and for a time of 30 minutes.

8. Process according to claim 4, wherein the reaction is carried out at a temperature of 0° C. and for a time of 2 hours.

9. Process according to claim 1, wherein the reduction reaction in step (b) is carried out in the liquid phase, in an inert organic solvent, in the presence of a reducing agent, and operating at a temperature of from 20° C. to +40° C. and for a time of from 20 minutes to 12 hours.

10. Process according to claim 9, wherein the solvent is selected from alcohols.

11. Process according to claim 10, wherein the solvent is ethanol or methanol.

12. Process according to claim 9, wherein the reduction agent is selected among the hydrides of alkali metals.

13. Process according to claim 12, wherein the reduction agent is sodium borohydride.

14. Process according to claim 1, wherein in step (c) the separation is carried out by crystallization from ethyl acetate.

15. Process according to claim 1, wherein the methanolysis reaction in step (d) is carried out in liquid medium, in methanol, in the presence of hydrogen chloride gas, at the boiling temperature, for a time of 24 hours.

16. Process according to claim 1, wherein in step (e) the separation of the methylester of the optically-active aminoacid (III) is carried out by precipitation by ethyl ether.

* * * * *